(12) United States Patent
Merslavic et al.

(10) Patent No.: US 8,470,869 B2
(45) Date of Patent: Jun. 25, 2013

(54) SALTS OF PERINDOPRIL

(75) Inventors: Marjo Merslavic, Straza Pri Novem Mestu (SI); Sergeja Bombek, Novo Mesto (SI); Urska Gojak, Ljubljana (SI); Matej Smrkolj, Trbovlje (SI); Rok Zupet, Ljubljana (SI)

(73) Assignee: KRKA, Tovarna Zdravil D.D. Novo Mesto, Novo Mesto (SI)

( * ) Notice: Subject to any disclaimer, the term of this patent is extended or adjusted under 35 U.S.C. 154(b) by 292 days.

(21) Appl. No.: 12/666,187

(22) PCT Filed: Jun. 27, 2008

(86) PCT No.: PCT/EP2008/058258
§ 371 (c)(1),
(2), (4) Date: Jun. 17, 2010

(87) PCT Pub. No.: WO2009/000909
PCT Pub. Date: Dec. 31, 2008

(65) Prior Publication Data
US 2010/0298400 A1  Nov. 25, 2010

(30) Foreign Application Priority Data
Jun. 27, 2007  (SI) .................................. 200700152

(51) Int. Cl.
*A61K 31/405* (2006.01)
*C07D 209/34* (2006.01)

(52) U.S. Cl.
USPC ......................................... 514/419; 548/419

(58) Field of Classification Search
USPC ....................................................... 548/416
See application file for complete search history.

(56) References Cited

U.S. PATENT DOCUMENTS

| | | | |
|---|---|---|---|
| 4,508,729 A * | 4/1985 | Vincent et al. ................. | 514/419 |
| 4,914,214 A | 4/1990 | Vincent et al. | |
| 6,653,336 B1 | 11/2003 | Guez et al. | |
| 2003/0158121 A1 | 8/2003 | Pfeiffer et al. | |
| 2003/0186896 A1 | 10/2003 | Pfeiffer et al. | |
| 2004/0029813 A1 | 2/2004 | Pfeiffer et al. | |
| 2007/0135512 A1 | 6/2007 | Strassler et al. | |

FOREIGN PATENT DOCUMENTS

| | | |
|---|---|---|
| EP | 49 658 | 4/1982 |
| EP | 308 341 | 3/1989 |
| EP | 1 294 689 | 3/2003 |
| EP | 1 296 947 | 4/2003 |
| EP | 1 296 948 | 4/2003 |
| EP | 1 647 547 | 4/2006 |
| FR | 2 771 010 | 5/1999 |
| GB | 2 394 660 | 5/2004 |
| GB | 2 395 195 | 5/2004 |
| JP | 2006169169 | 6/2006 |
| JP | 2006290825 | 10/2006 |
| RU | 2 280 450 | 6/2006 |
| RU | 2 282 443 | 6/2006 |
| SI | 21801 | 6/2004 |
| WO | WO0183439 | 11/2001 |
| WO | WO0187835 | 11/2001 |
| WO | WO0187836 | 11/2001 |
| WO | WO 2004046172 | 6/2004 |
| WO | WO2004113293 | 12/2004 |
| WO | WO2005037788 | 4/2005 |
| WO | WO 2005068425 | 7/2005 |
| WO | WO 2005068490 | 7/2005 |
| WO | WO 2005094793 | 10/2005 |
| WO | WO 2005113500 | 12/2005 |
| WO | WO 2006097941 | 9/2006 |
| WO | WO 2006101462 | 9/2006 |
| WO | WO 2007017087 | 2/2007 |
| WO | WO 2007017893 | 2/2007 |
| WO | WO 2007017894 | 2/2007 |
| WO | WO 2007020009 | 2/2007 |
| WO | WO 2007020012 | 2/2007 |
| WO | WO 2007025695 | 3/2007 |
| WO | WO 2007058634 | 5/2007 |
| WO | WO 2007062865 | 6/2007 |
| WO | WO 2008150245 | 12/2008 |
| WO | WO2008150245 A2 * | 12/2008 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Document No. 150:41316, retrieved from CAPLUS (2008).*
English Abstract corresponding to foreign patent RU 2280450 published on Jun. 10, 2006, espacenet.com, 1 page.
English Abstract corresponding to foreign patent RU 2282443 published on Jun. 10, 2006, espacenet.com, 1 page.
Berge et al., "Pharmaceutical Salts," Journal of Pharmaceutical Sciences, vol. 66, No. 1, Jan. 1977, pp. 1-19.
Gould, "Salt Selection for Basic Drugs, International Journal of Pharmaceutics," vol. 33, 1986, pp. 201-217.
International Search Report dated Jan. 28, 2010, in corresponding PCT/EP08/58258, 8 pages.
English translation of abstract corresponding to foreign patent EP 49658 published on Apr. 14, 1982, espacenet.com, 1 page.
English translation of abstract corresponding to foreign patent JP 2006169169 published on Jun. 29, 2006, espacenet.com, 1 page.
English translation of abstract corresponding to foreign patent JP 2006290825 published on Oct. 26, 2006, espacenet.com, 1 page.
English translation of abstract corresponding to foreign patent SI 21801 published on Jun. 21, 2004, espacenet.com, 1 page.

* cited by examiner

*Primary Examiner* — Shawquia Young
(74) *Attorney, Agent, or Firm* — Hovey Williams LLP

(57) ABSTRACT

The present invention relates to new salts of perindopril, particularly to a new calcium salt and new amine salts of perindopril, to a process for their preparation and to a pharmaceutical formulations containing the new salts.

19 Claims, 17 Drawing Sheets

SALTS OF PERINDOPRIL

RELATED APPLICATIONS

This application claims priority to PCT International Patent Application No. PCT/EP2008/058258, filed Jun. 27, 2008, which claims the priority benefit of Slovenia Patent Application No. 200700152, filed Jun. 27, 2007, both of which are hereby incorporated by reference in their entirety.

TECHNICAL FIELD

The present invention belongs to the field of organic chemistry and relates to new salts of perindopril, a process for the preparation of the new salts and pharmaceutical compositions including these salts. Perindopril is a compound having ACE inhibitory activity.

Technical Problem

There existed a need for new salts of perindopril that could be prepared in a simple and industrially acceptable manner and could be used in the preparation of new pharmaceutical compositions providing an appropriate bioavailabity and stability of the product.

Prior Art

Perindopril with its chemical name (2S,3aS,7aS)-1-((2S)-2-(((1S)-1-ethoxycarbonyl)butyl)amino-1-oxopropyl)octahydro-1H-indole-2-carboxylic acid is described in EP 49 658. The synthesis is a multistage one and includes a resolution of the isomers by column chromatography. EP 308 341 discloses an improved synthesis of perindopril in the form of t-butylamine salt on an industrial scale. The synthesis involves the reaction between the p-toluenesulfonic salt of (2S,3aS,7aS)-octahydroindole-2-carboxylic acid benzyl ester and N—((S)-1-carbetoxybutyl)-L-alanine in the presence of triethylamine, N,N-dicyclohexylcarbodiimide and 1-hydroxybenzotriazole. After completion of the reaction a benzyl ester of perindopril is obtained, which is then reduced, lyophilized and converted to the salt with t-butylamine in ethyl acetate.

Polymorphic forms of the t-butylamine salt of perindopril are disclosed in EP 1 296 947, which discloses the alpha form prepared from ethyl acetate, in EP 1 294 689, which discloses the beta form prepared from dichloromethane or ethyl acetate, in EP 1 296 948, which discloses the gamma form prepared from chloroform. In the patent application WO 2004/113293, the company Azad discloses new delta and epsilon forms prepared by crystallization from t-butyl methyl ether containing from 0.9% to 2.5% (v/v) of water.

Crystallizations from different solvents and characterizations of polymorphs are also disclosed in WO 2005/37788 of Lupin.

In GB 2 395 195 and WO 2004/46172, the company Cipla discloses perindopril t-butylamine monohydrate. In EP 1 647 547 of the company Diagen, hydrate forms prepared by lyophilization are disclosed. The preparation of polymorphs is also disclosed in JP 2006-169169, JP 2006-290825, S121801, WO 2005/68425, WO 2007/17894, WO 2007/17893, WO 2007/20012, WO 2007/17087 and WO 2007/20009.

Amine salts of perindopril are also disclosed in WO 2006/97941 and WO 2007/17087.

Formulations of perindopril are disclosed in WO 2005/94793, WO 2005/68490, WO 2006/101462, WO 2007/25695, WO 2007/58634, RU 2 280 450 and RU 2 282 443.

It has now been found that the new salts according to the present invention are surprisingly stable and useful for the preparation of pharmaceutical formulations.

X-ray powder diffractograms were obtained by a diffractometer Phillips PW3040/60 X'Pert PRO using $CuK_\alpha$-radiation 1.541874. FT-IR spectra were recorded with an FT-IR System Spectrum GX Perkin Elmer apparatus, resolution 4 $cm^{-1}$, range 4000-400 $cm^{-1}$ using KBr-discs. The particle size was determined by a Malvern Mastersizer instrument based on laser diffraction.

DETAILED DESCRIPTION OF THE INVENTION

An object of the present invention are new salts of perindopril, a process for their preparation and a pharmaceutical compositions containing the new salts.

In a first aspect the present invention relates to a calcium salt of perindopril or a solvate thereof.

The calcium salt of the present invention can be prepared according to a process comprising the reaction of perindopril, which may optionally be in the form of salts or hydrates, with calcium salts, such as halides, carbonates, sulfates, acetates, phosphates, and preferably with calcium chloride, in an organic solvent. Usually, the obtained reaction mixture is heated to a temperature from 30° C. to the boiling point of the mixture, then cooled and the product is isolated. The mixture is preferably cooled to a temperature from 25° C. to −5° C., and in particular from 25° C. to 0° C. Cooling can be effected using conventional cooling measures, including leaving to stand at room temperature, and carried out under stirring or without stirring.

As the organic solvent nitriles, esters, hydrocarbons, halogenated hydrocarbons, ketones, ethers or mixtures of these solvents as well as mixtures of these solvents with water can be used. Preferably esters and nitriles, such as ethyl acetate and acetonitrile are used.

The calcium salt of the present invention may also be present in the form of an acid addition salt thereof with organic or inorganic acids, such as HCl, HBr, HI, maleic acid, and fumaric acid, and preferably with HCl.

Figure 1:
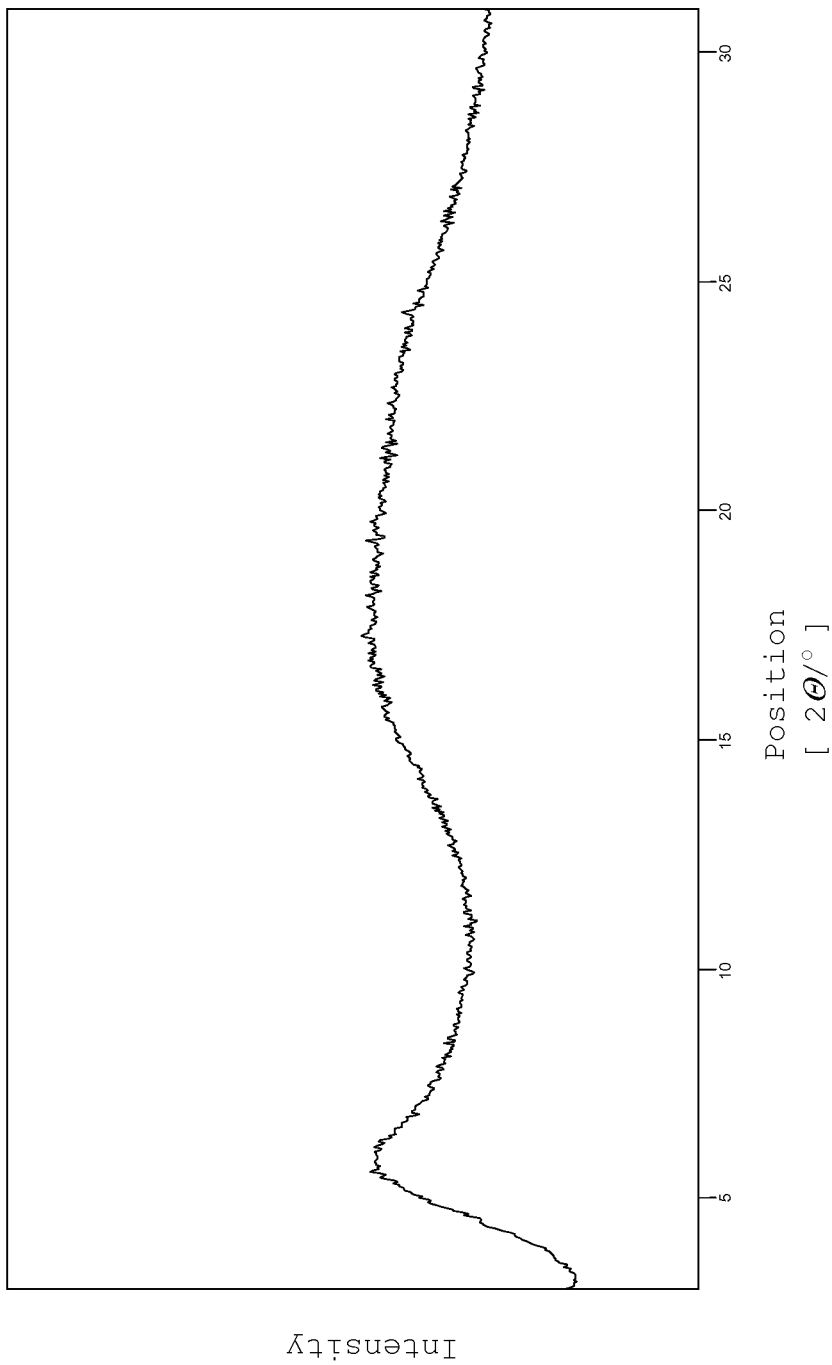
FIG. 1 is an X-ray powder diffractogram of Ca salt of perindopril hydrochloride.
Figure 2:
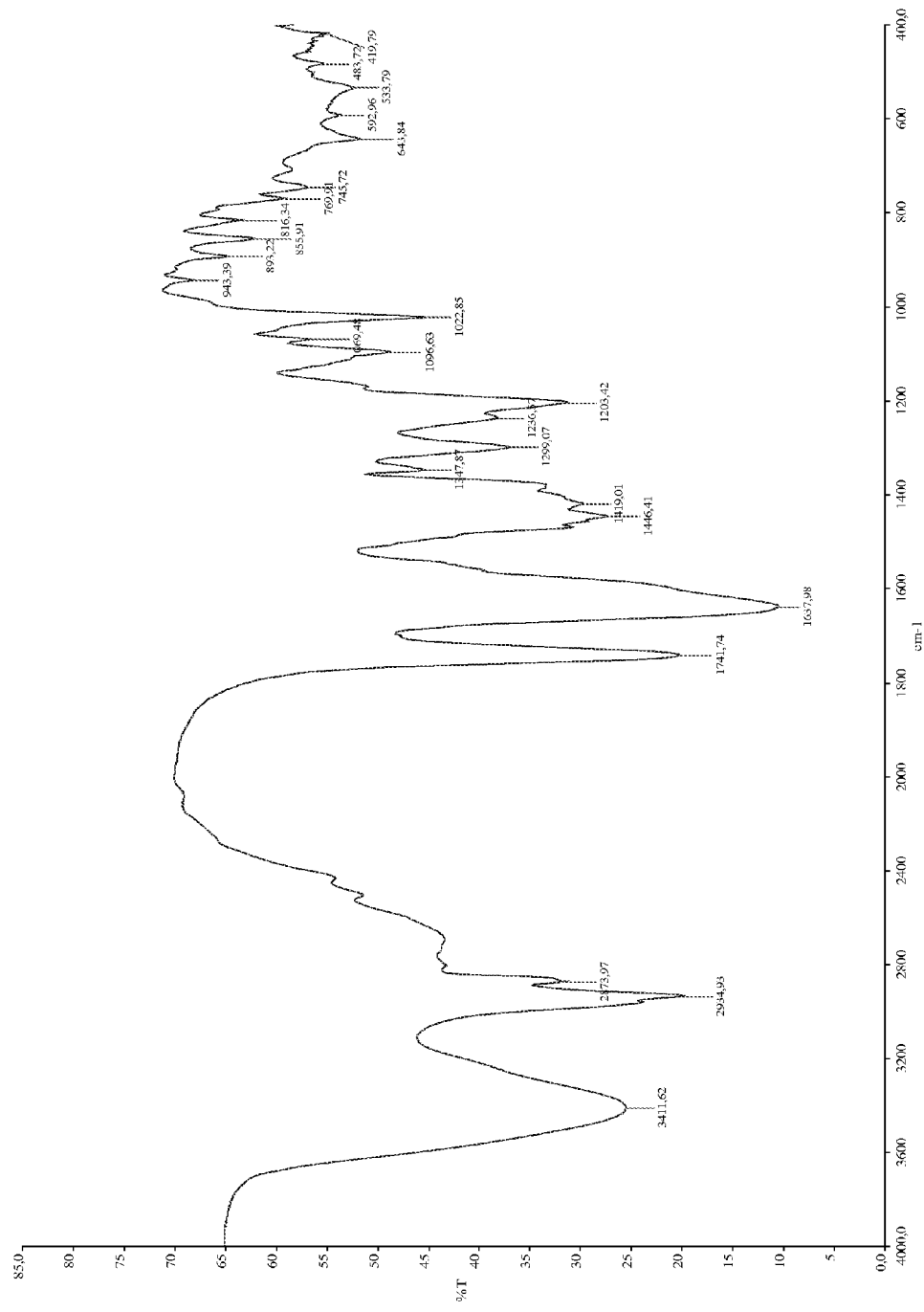
FIG. 2 is an FT-IR spectrum of Ca salt of perindopril hydrochloride.
Figure 3:
FIG. 3 shows a microscopical image of particles of Ca salt of perindopril hydrochloride.

The particularly preferred calcium salt of perindopril hydrochloride is also characterised by an X-ray powder diffraction pattern, which is substantially as represented in FIG. 1, or by an FT-IR spectrum, which is substantially as represented in FIG. 2.

The acid addition salts according to the invention can be prepared by reacting the calcium salt of perindopril in a suitable solvent with an organic or inorganic acid. A particularly preferred solvent is ethyl acetate.

Another aspect of the invention are new alkyl amine salts of perindopril represented by the structural formula:

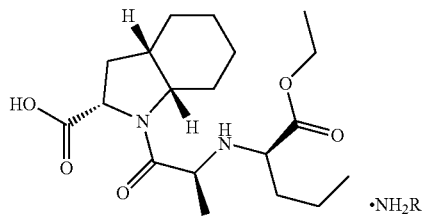

wherein R represents $C_5$-$C_7$ cycloalkyl or sec-butyl.

The group R is preferably cyclopentyl, cyclohexyl, cycloheptyl or sec-butyl.

The new salts according to the present invention can be prepared in the form of solvates, hydrates or in an anhydrous form. We have found that the alkyl amine salts of perindopril according to the invention can surprisingly be obtained in a stable crystal form, more specifically, they occur in a form having a great crystallinity. Further, the new salts show an exceptional chemical stability and thus they are useful for the preparation of stable pharmaceutical forms. Further, the salts according to the present invention can be used for the purification of perindopril.

A further aspect of the invention is a new cycloheptylamine salt of perindopril characterised by an X-ray powder diffraction pattern having peaks 2Θ/° at about (4.0, 9.0, 14.1, 15.2, 16.8, 18.1, 21.0, 24.1)±0.2. It is further characterised by an X-ray powder diffraction pattern and has peaks with relative intensities as represented in Table 1.

TABLE 1

| No. | Pos. [2Θ/°] | d-spacing [Å] | Rel. Int. [%] |
|---|---|---|---|
| 1 | 4.0 | 22.12 | 18 |
| 2 | 9.0 | 9.81 | 46 |
| 3 | 14.1 | 6.28 | 41 |
| 4 | 15.2 | 5.81 | 47 |
| 5 | 16.8 | 5.27 | 41 |
| 6 | 18.1 | 4.90 | 57 |
| 7 | 21.0 | 4.23 | 57 |
| 8 | 24.1 | 3.70 | 100 |

Figure 4:
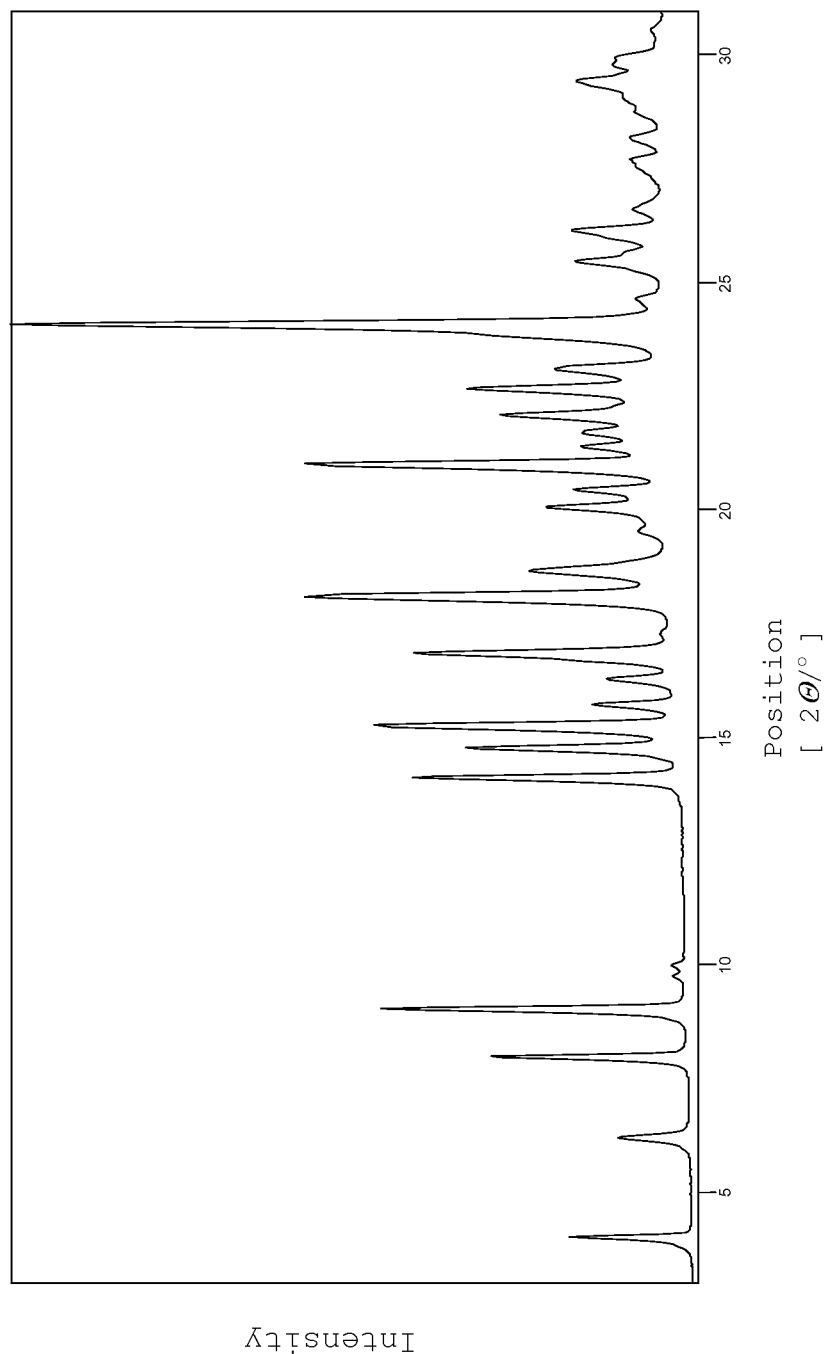
FIG. 4 is an X-ray powder diffractogram of cycloheptylamine salt of perindopril.
Figure 5:
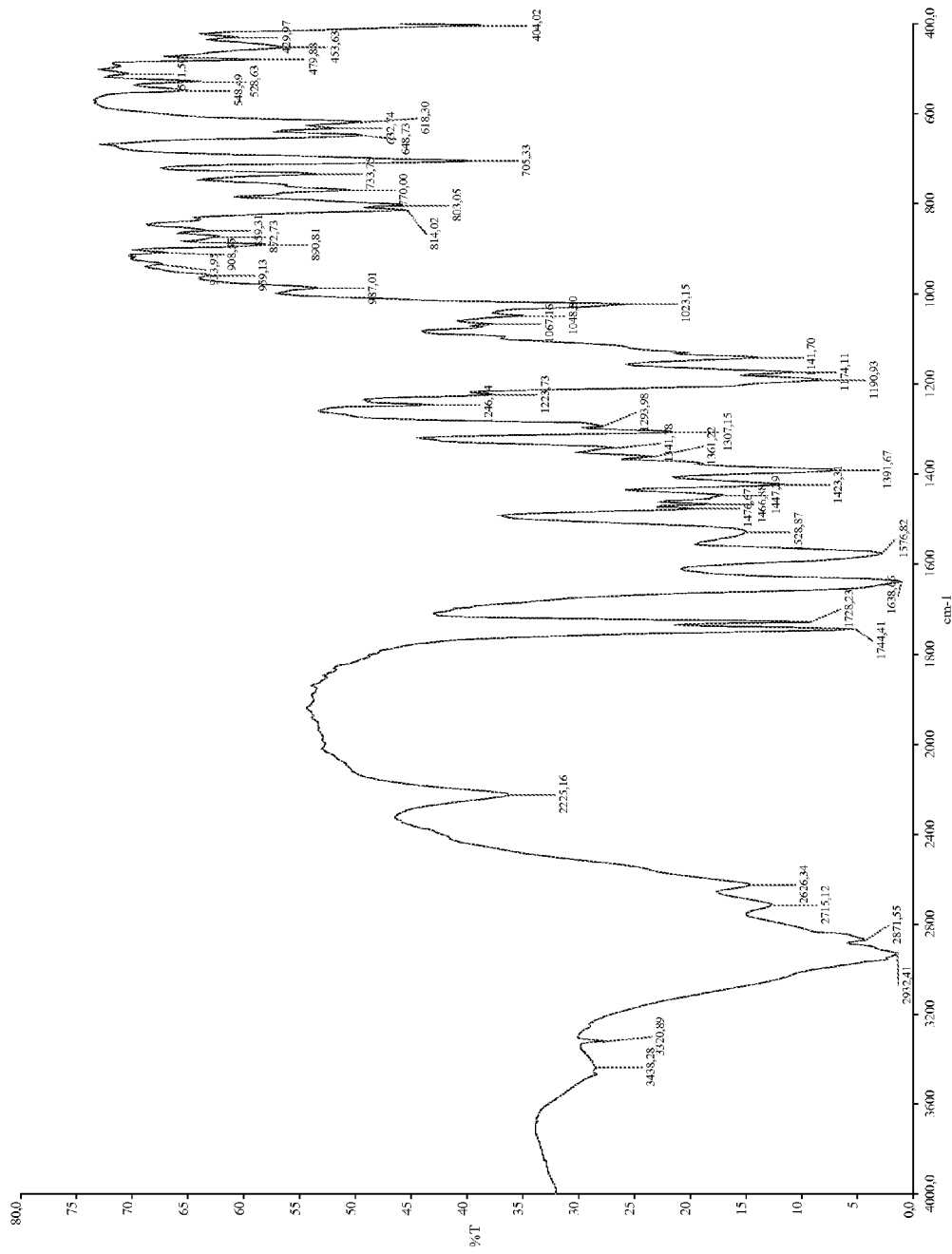
FIG. 5 is an FT-IR spectrum of cycloheptylamine salt of perindopril.
Figure 6:
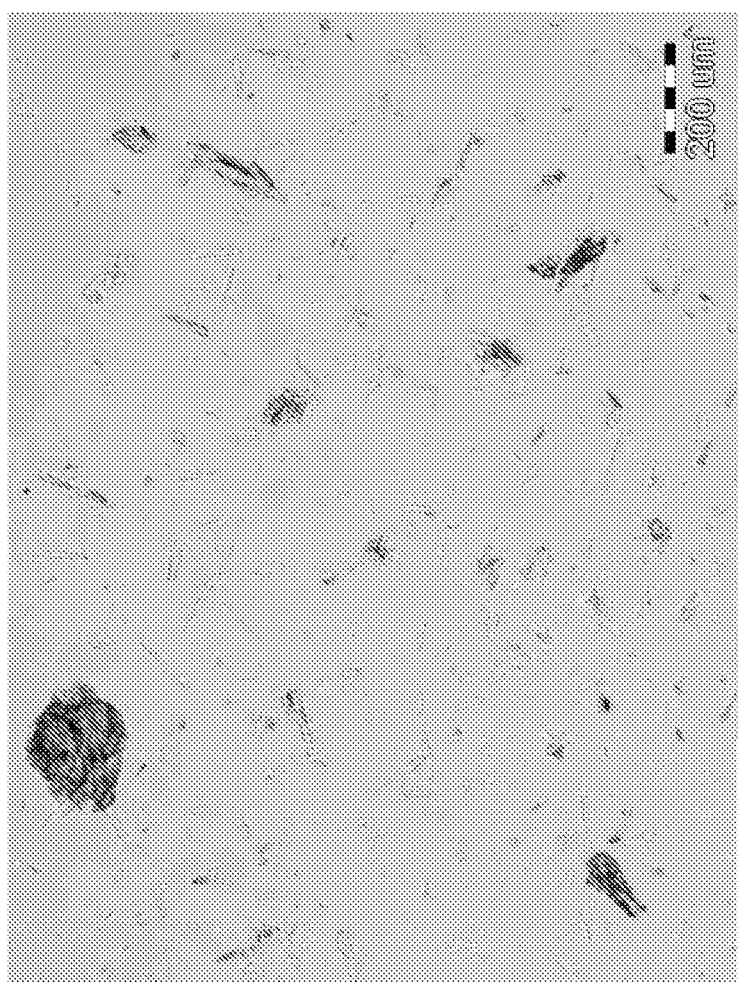
FIG. 6 shows a microscopical image of particles of cycloheptylamine salt of perindopril.

The cycloheptylamine salt according to the invention is further characterised by an X-ray powder diffractogram as substantially represented in FIG. 4 or by an FT-IR spectrum as substantially represented in FIG. 5.

A further aspect of the invention is a new cyclohexylamine salt of perindopril characterised by an X-ray powder diffraction pattern having peaks 2Θ/° at about (4.1, 8.1, 9.3, 15.2, 18.8, 21.1, 22.2, 24.3)±0.2. It is further characterised by an X-ray powder diffraction pattern and has peaks with relative intensities as represented in Table 2.

TABLE 2

| No. | Pos. [2Θ/°] | d-spacing [Å] | Rel. Int. [%] |
|---|---|---|---|
| 1 | 4.1 | 21.79 | 13 |
| 2 | 8.1 | 10.95 | 25 |
| 3 | 9.3 | 9.50 | 13 |
| 4 | 15.2 | 5.84 | 17 |
| 5 | 18.8 | 4.73 | 17 |
| 6 | 21.1 | 4.22 | 14 |
| 7 | 22.2 | 4.01 | 12 |
| 8 | 24.3 | 3.66 | 100 |

Figure 7:
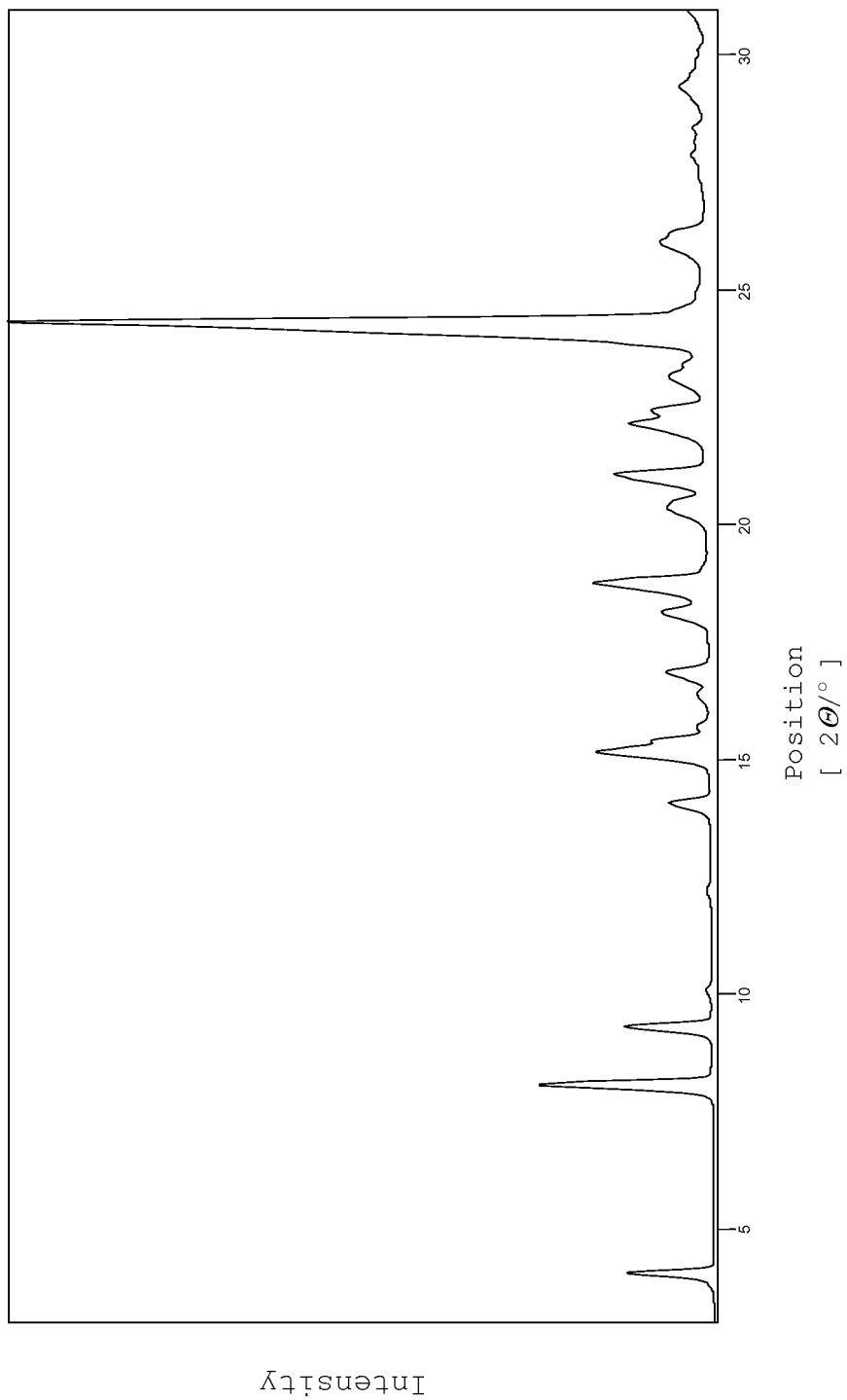
FIG. 7 is an X-ray powder diffractogram of cyclohexylamine salt of perindopril.
Figure 8:
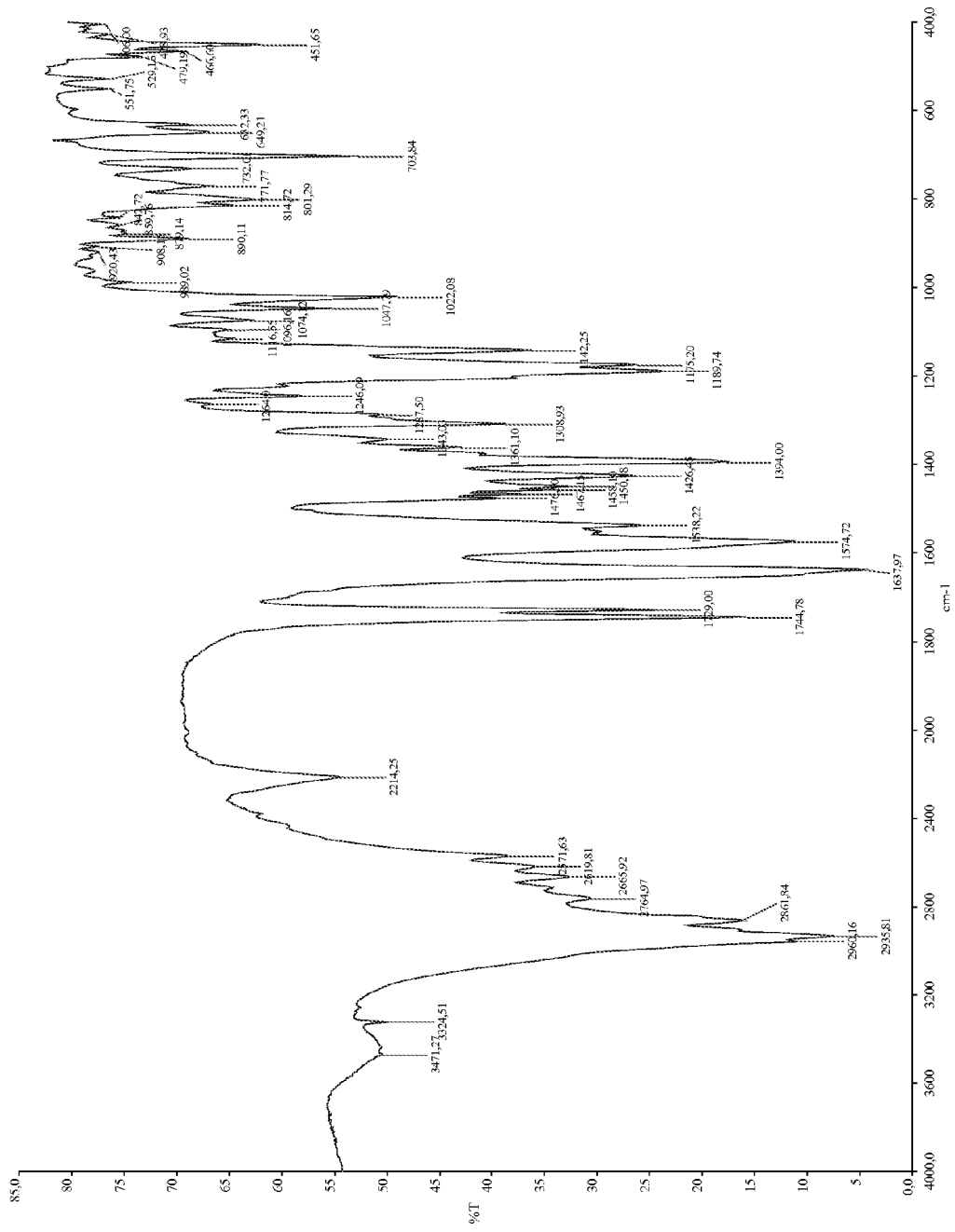
FIG. 8 is an FT-IR spectrum of cyclohexylamine salt of perindopril.
Figure 9:
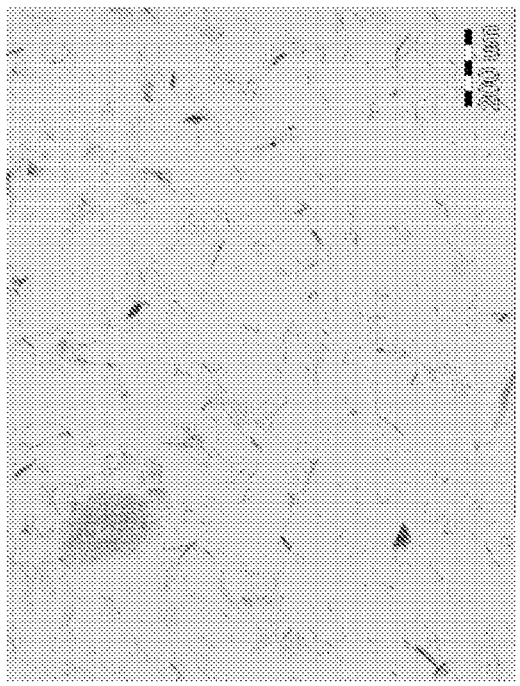
FIG. 9 shows two microscopical images of particles of cyclohexylamine salt of perindopril differing in particle size.
Figure 9:
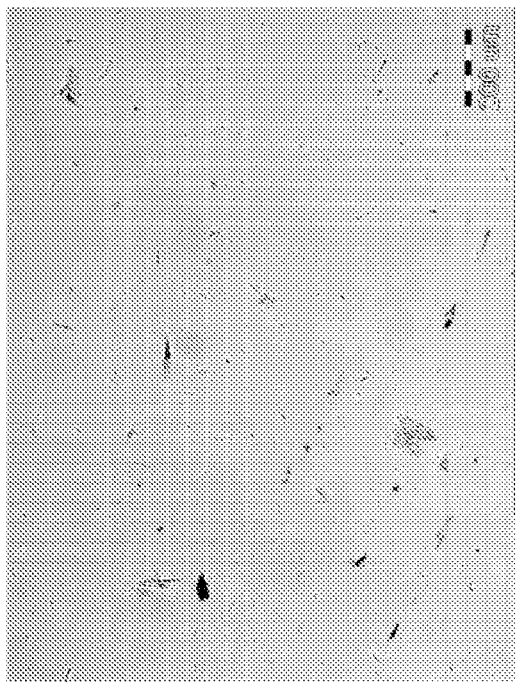

The cyclohexylamine salt according to the invention is further characterised by an X-ray powder diffractogram as substantially represented in FIG. 7 or by an FT-IR spectrum as substantially represented in FIG. 8.

A further aspect of the invention is a new cyclopentylamine salt of perindopril characterised by an X-ray powder diffraction pattern having peaks 2Θ/° at about (8.1, 9.2, 16.9, 19.1, 19.8, 21.3, 22.8, 24.4)±0.2. It is further characterised by an X-ray powder diffraction pattern and has peaks with relative intensities as represented in Table 3.

TABLE 3

| No. | Pos. [2Θ/°] | d-spacing [Å] | Rel. Int. [%] |
|---|---|---|---|
| 1 | 8.1 | 10.92 | 21 |
| 2 | 9.2 | 9.59 | 100 |
| 3 | 16.9 | 5.26 | 34 |
| 4 | 19.1 | 4.64 | 47 |
| 5 | 19.8 | 4.49 | 24 |
| 6 | 21.3 | 4.18 | 39 |
| 7 | 22.8 | 3.91 | 31 |
| 8 | 24.4 | 3.65 | 65 |

Figure 10:
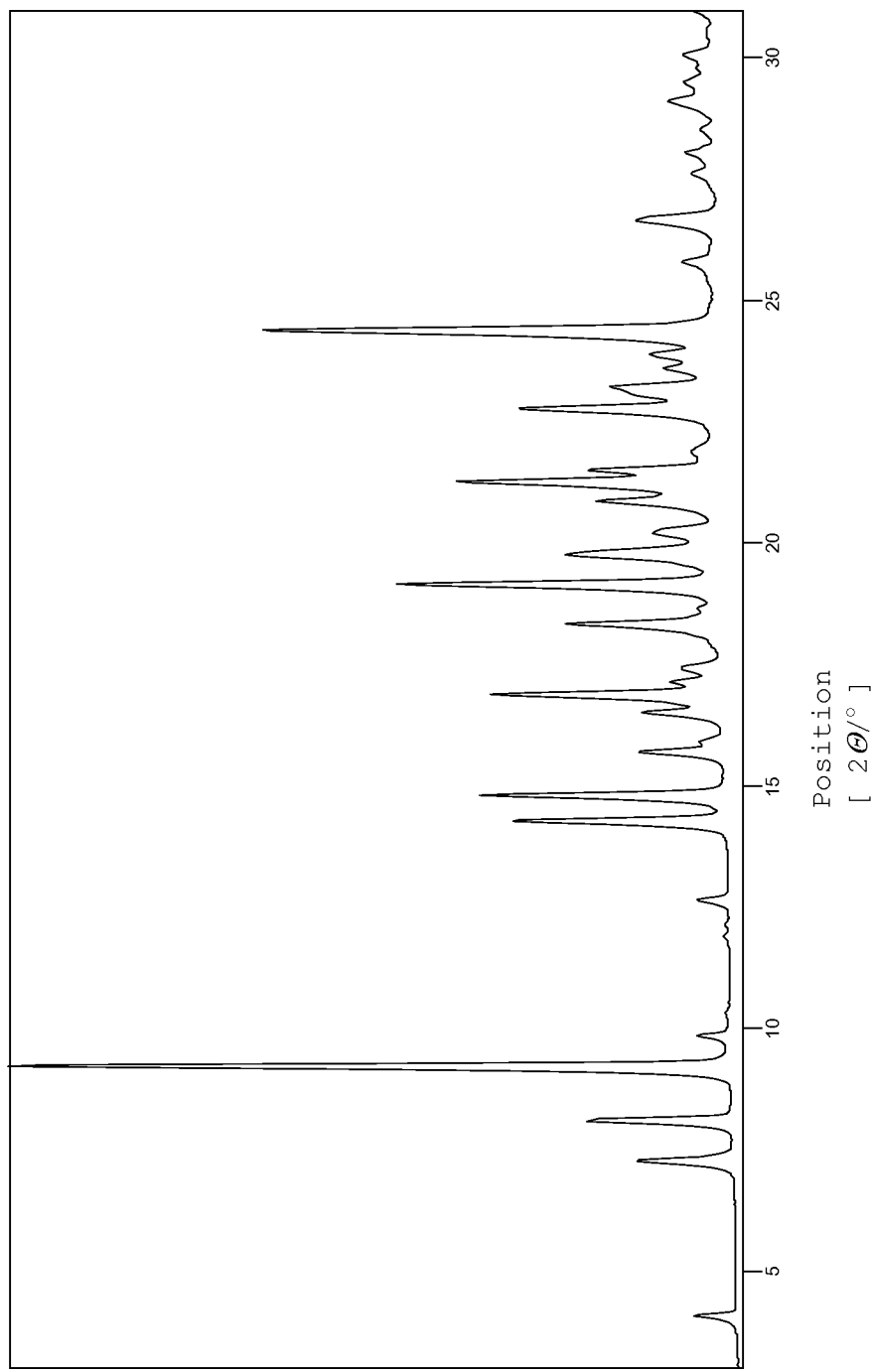
FIG. 10 is an X-ray powder diffractogram of cyclopentylamine salt of perindopril.
Figure 11:
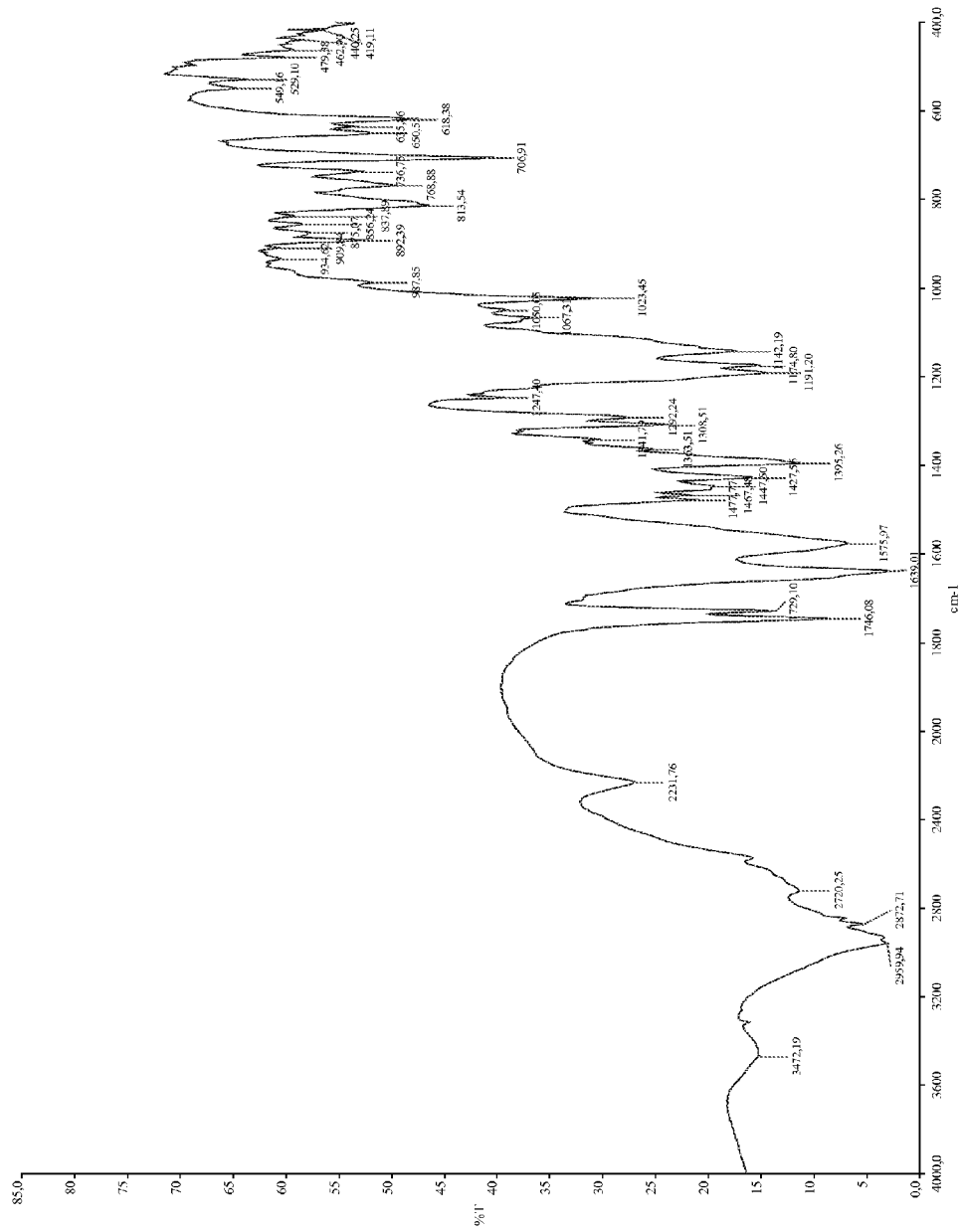
FIG. 11 is an FT-IR spectrum of cyclopentylamine salt of perindopril.
Figure 12:
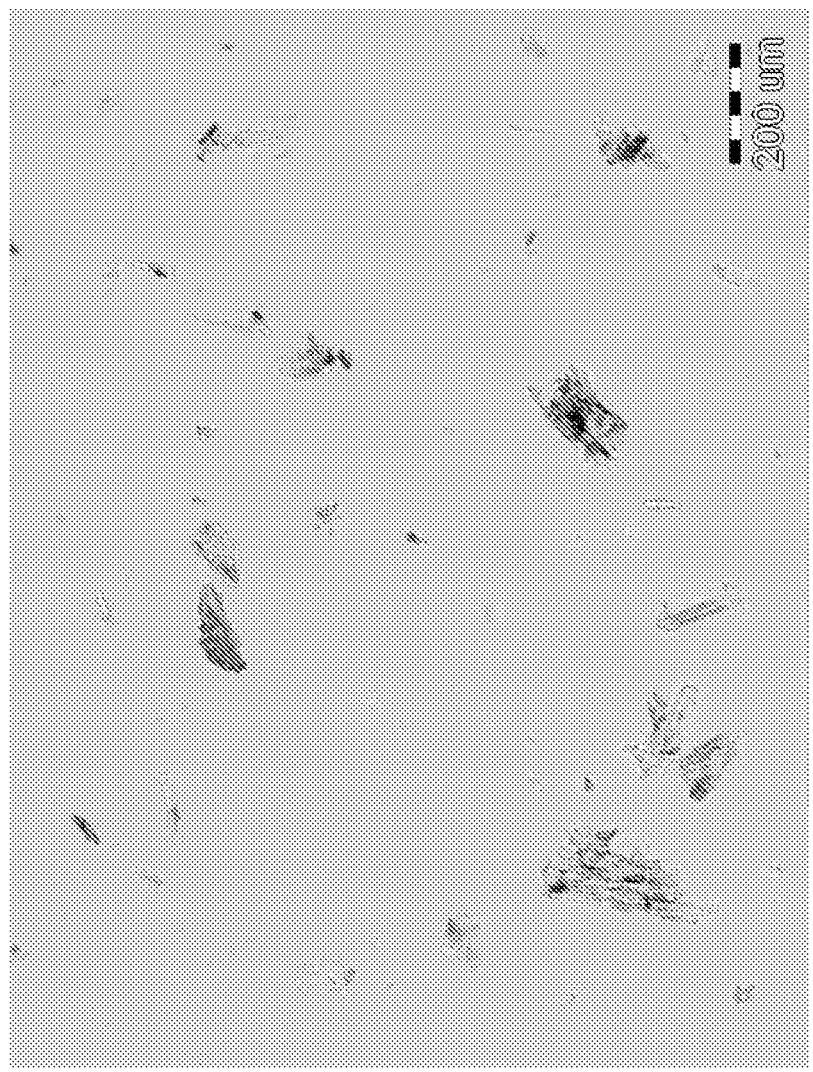
FIG. 12 shows a microscopical image of particles of cyclopentylamine salt of perindopril.

The cyclopentylamine salt according to the invention is further characterised by an X-ray powder diffractogram as substantially represented in FIG. 10 or by an FT-IR spectrum as substantially represented in FIG. 11.

A further aspect of the invention is a new sec-butylamine salt of perindopril characterised by an X-ray powder diffraction pattern having peaks 2Θ/° at about (5.0, 8.6, 9.3, 15.3, 20.4, 20.8, 22.4, 24.2, 26.1)±0.2. It is further characterised by an X-ray powder diffraction pattern and has peaks with relative intensities as represented in Table 4.

TABLE 4

| No. | Pos. [2Θ/°] | d-spacing [Å] | Rel. Int. [%] |
|---|---|---|---|
| 1 | 5.0 | 17.50 | 5 |
| 2 | 8.6 | 10.29 | 23 |
| 3 | 9.3 | 9.47 | 100 |
| 4 | 15.3 | 5.80 | 45 |
| 5 | 20.4 | 4.35 | 29 |
| 6 | 20.8 | 4.26 | 19 |
| 7 | 22.4 | 3.98 | 34 |
| 8 | 24.2 | 3.68 | 40 |
| 9 | 26.1 | 3.42 | 10 |

Figure 13:
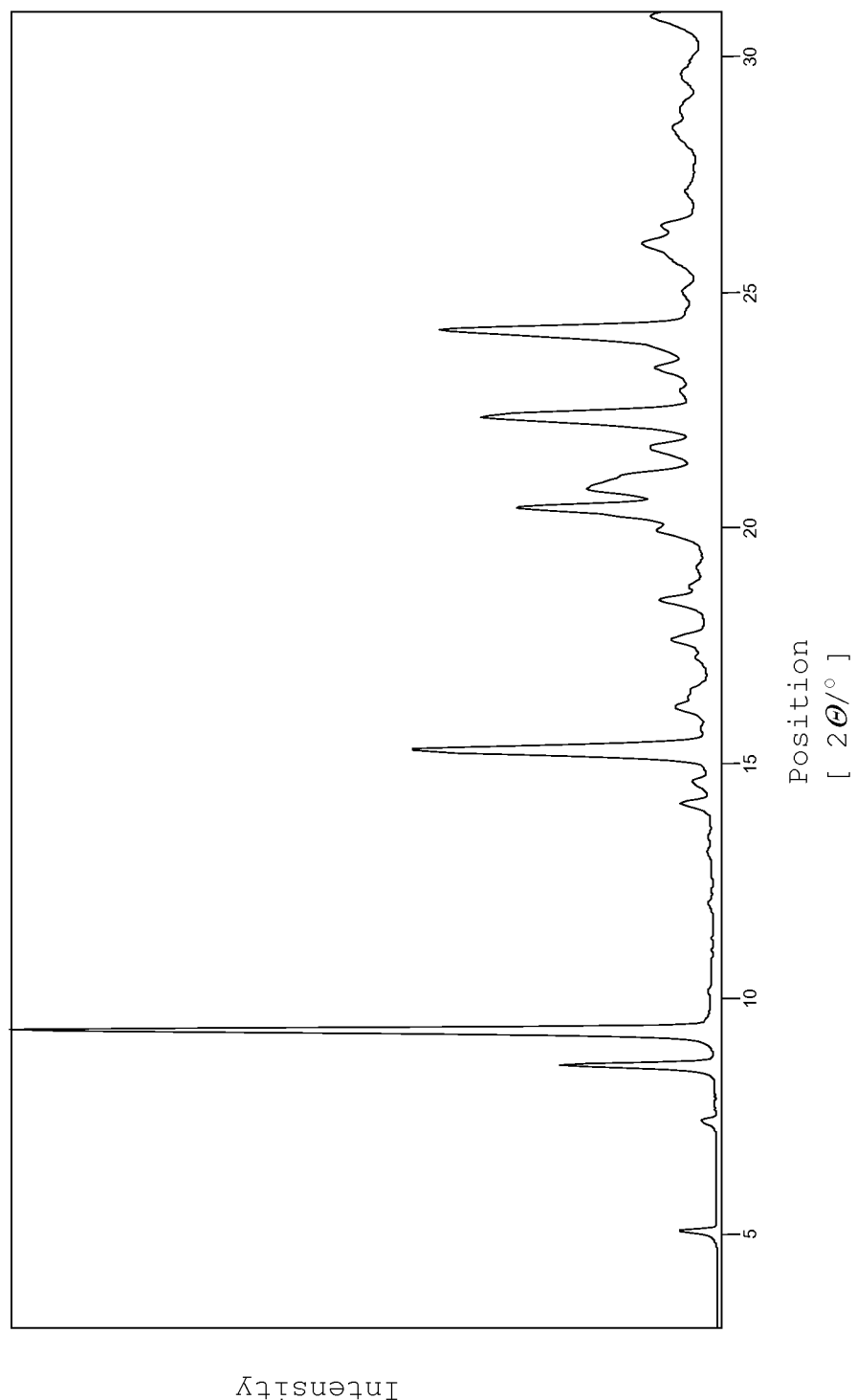
FIG. 13 is an X-ray powder diffractogram of sec-butylamine salt of perindopril.
Figure 14:
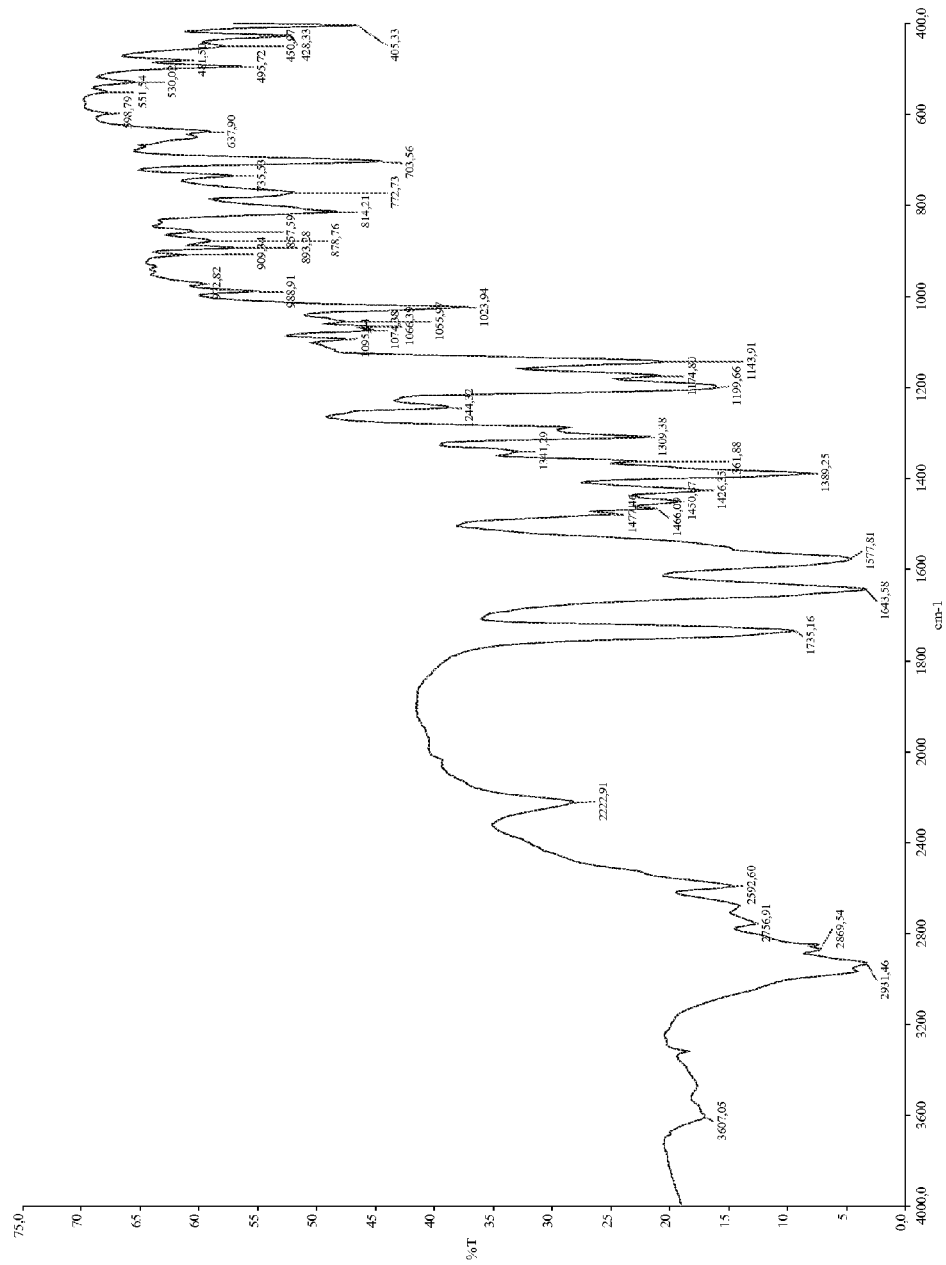
FIG. 14 is an FT-IR spectrum of sec-butylamine salt of perindopril.
Figure 15:
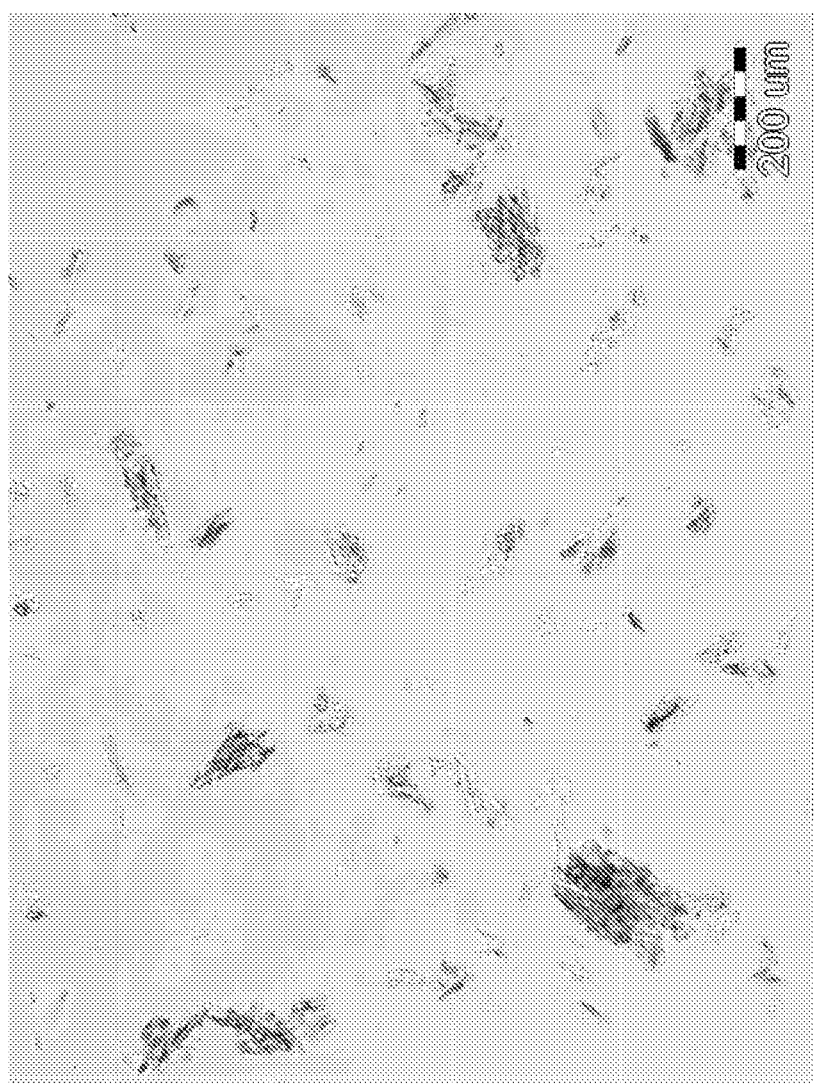
FIG. 15 shows a microscopical image of particles of sec-butylamine salt of perindopril.

The sec-butylamine salt of perindopril according to the invention is further characterised by an X-ray powder diffractogram as substantially represented in FIG. 13 or by an FT-IR spectrum as substantially represented in FIG. 14.

A further object of the invention is also a process for the preparation of the amine salts of perindopril of the invention comprising the addition of an appropriate amine to a solution of perindopril in an organic solvent, heating the obtained reaction mixture to a temperature between 30° C. and the boiling point of the reaction mixture, cooling the reaction mixture and isolating the product.

As the organic solvent nitriles, esters, hydrocarbons, halogenated hydrocarbons, ketones, ethers or mixtures of these solvents as well as mixtures of these solvents with water can be used. Preferably esters and nitriles, such as ethyl acetate and acetonitrile are used.

In particular, the mixture is cooled to a temperature from 25° C. to −5° C., preferably from 25° C. to 0° C. After cooling to the desired temperature, the crystallization mixture is in particular further stirred at this temperature for further 15 minutes to 24 hours, preferably from 1 to 12 hours.

In a preferred embodiment, the precipitated product is isolated and dried at reduced pressure, preferably from 30 mbar to 100 mbar and at a temperature below 50° C., preferably at a temperature from 30° C. to 45° C. It is usually dried until a constant weight of the product. The water content in the product after drying is, in the case of anhydrous product, less than 1%, preferably less than 0.5% and, in the case of hydrates, less than 5%, preferably less than 4%.

A further aspect of the invention is a new polymorphic form M1 of perindopril erbumine, characterised by an X-ray powder diffraction pattern having peaks 2Θ/° at about (4.2, 16.6, 21.1, 21.6, 25.4, 27.2)±0.2. It is further characterised by an X-ray powder diffraction pattern and has peaks with relative intensities as represented in Table 5.

TABLE 5

| No. | Pos. [2Θ/°] | d-spacing [Å] | Rel. Int. [%] |
|---|---|---|---|
| 1 | 4.2 | 21.06 | 25 |
| 2 | 16.6 | 5.33 | 100 |
| 3 | 21.1 | 4.21 | 16 |
| 4 | 21.6 | 4.11 | 9 |
| 5 | 25.4 | 3.51 | 4 |
| 6 | 27.2 | 3.28 | 13 |

Figure 16:
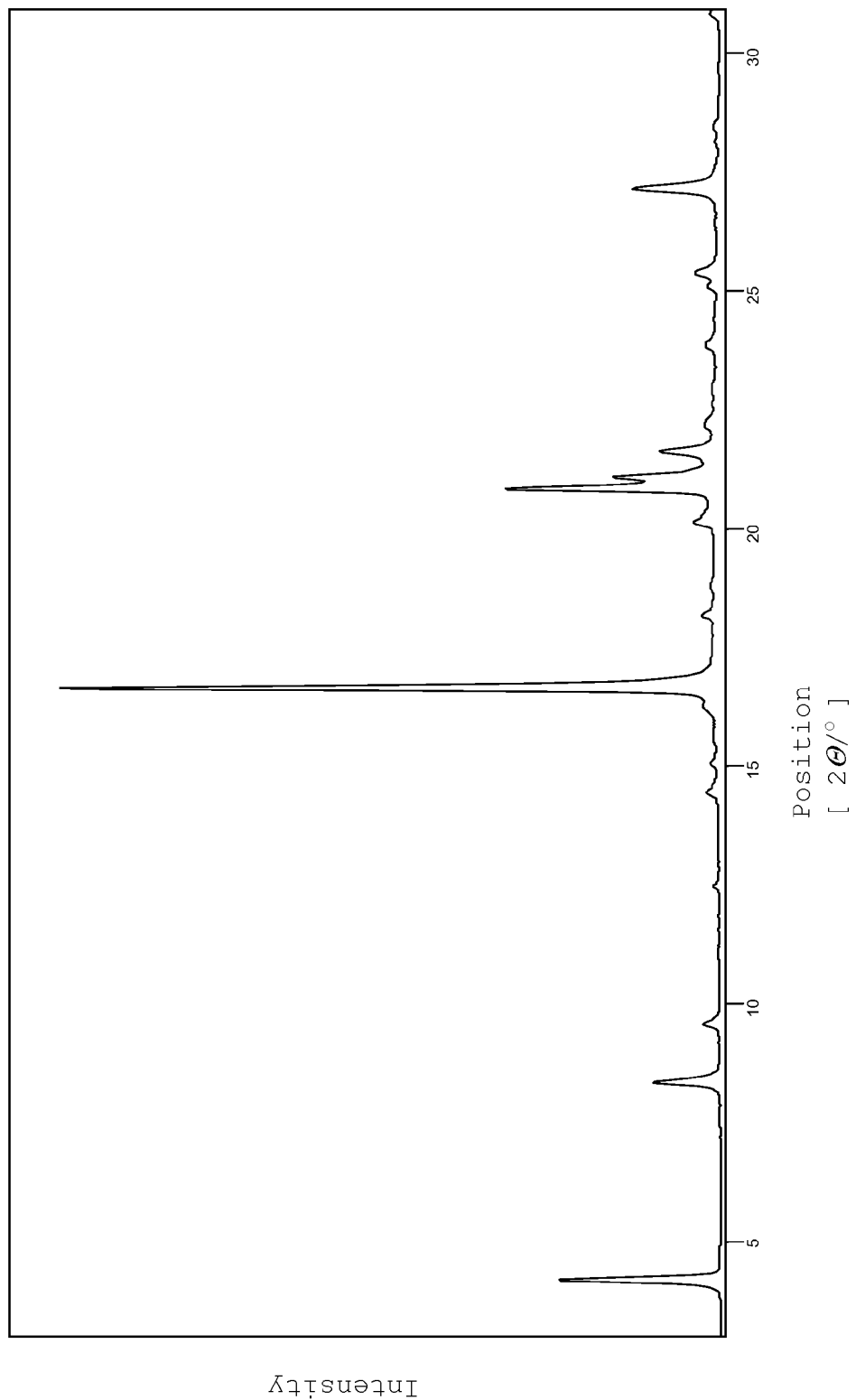
FIG. 16 is an X-ray powder diffractogram of polymorphic form M1 of perindopril erbumine.

The new polymorphic form M1 of perindopril erbumine is further characterized by an X-ray powder diffractogram as substantially represented in FIG. 16.

The polymorphic form M1 of perindopril erbumine is prepared by maceration in acetonitrile or ethyl acetate. The maceration is preferably carried out for about 10 hours.

A further aspect of the invention is a new polymorphic form M2 of perindopril erbumine, characterized by an X-ray powder diffraction pattern having peaks 2Θ/° at about (4.2, 16.6, 20.8, 25.0, 29.3)±0.2. It is further characterised by an X-ray powder diffraction pattern and has peaks with relative intensities as represented in Table 6.

TABLE 6

| No. | Pos. [2Θ/°] | d-spacing [Å] | Rel. Int. [%] |
|---|---|---|---|
| 1 | 4.2 | 20.97 | 15 |
| 2 | 16.6 | 5.33 | 100 |
| 3 | 20.8 | 4.27 | 65 |
| 4 | 25.0 | 3.56 | 20 |
| 5 | 29.3 | 3.05 | 5 |

Figure 17:
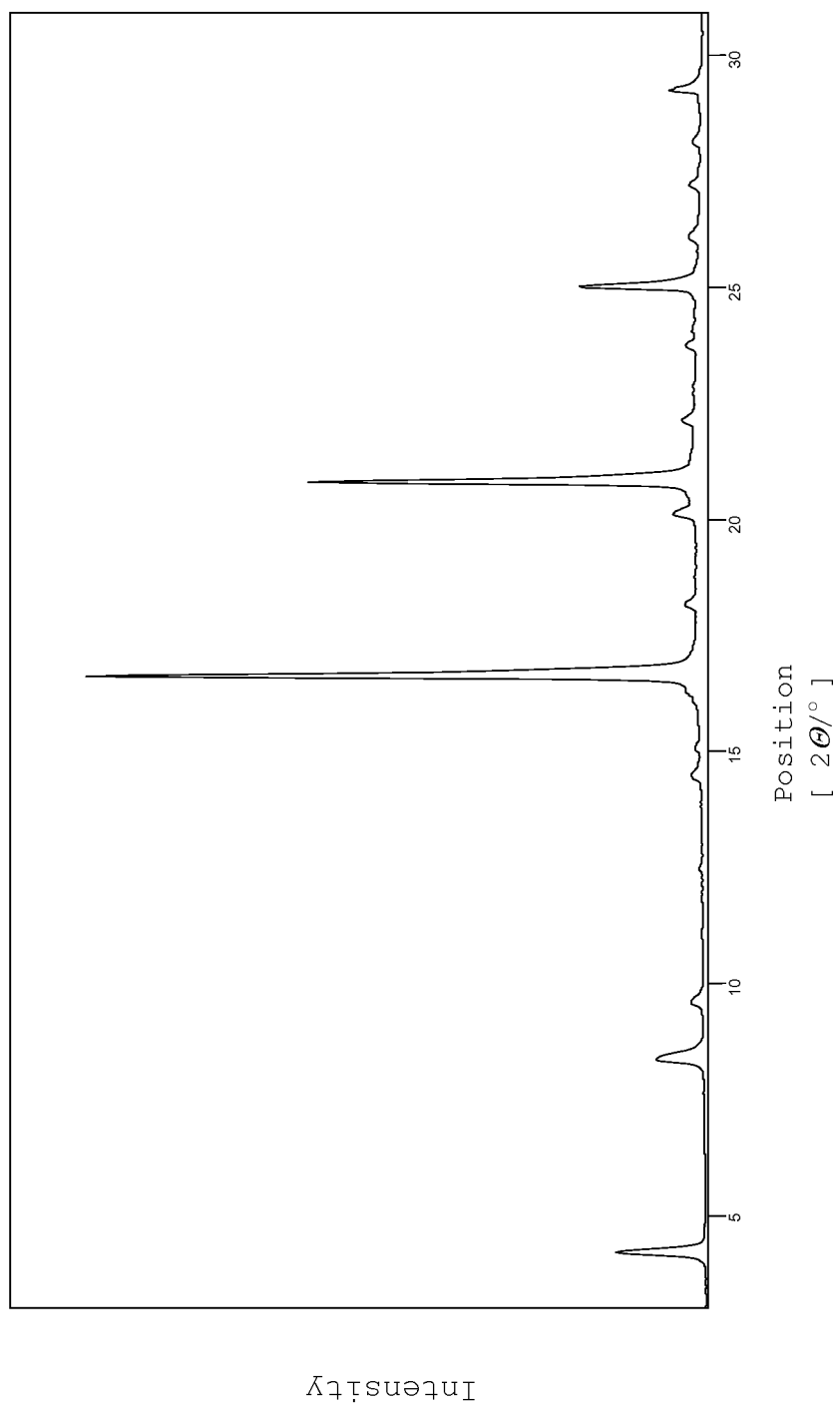
FIG. 17 is an X-ray powder diffractogram of polymorphic form M2 of perindopril erbumine.

The new polymorphic form M2 of perindopril erbumine is further characterized by an X-ray powder diffractogram as substantially represented in FIG. 17.

The polymorphic form M2 is obtained by storing the form M1 under closed conditions at room temperature for a prolonged period, in particular about 7 months. The storing is preferably conducted in a closed glass container.

The particle size of the perindopril salts prepared according to the present invention can be in the range 0.1-300 μm, preferably 5-150 μm, most preferably 20-100 μm. The size of the prepared particles depends on the rate of cooling the solution. If smaller particles are required, they can be milled or micronized, optionally with other excipients.

As the perindopril used as starting material there can be employed a crude product obtained according to any known process, e.g. by the synthesis processes as described in WO 05/113500 and WO 2007/62865, or any known polymorphic form as well as solvates or hydrates of perindopril and other salts of perindopril.

The new salts of perindopril according to the present invention can be used as a therapeutically active substance, which together with a pharmaceutically acceptable carrier can be used as a medicament. This medicament can be used for the treatment of cardiovascular diseases, especially for the treatment of hypertension and cardial insufficiency.

A further object of the present invention is a pharmaceutical composition containing the new amine salts of perindopril or the calcium salt of perindopril of the present invention as well as their combinations with indapamide or amlodipine or salts thereof. As pharmaceutically acceptable auxiliaries, substances generally known to someone skilled in the field of pharmacy can be used.

The pharmaceutical formulation can be prepared by processes known to someone skilled in the field of pharmacy, such as direct compacting, dry granulation or wet granulation.

Pharmaceutical formulations containing the new salts of the present invention can be prepared according to the Examples described in the prior art such as WO 2005/094793, FR 2 771 010 and GB 2 394 660.

Pharmaceutical formulations according to the present invention contain at least one auxiliary selected from the group of fillers or carriers, binders, disintegrants, stabilizers, lubricants, glidants, surfactants, sweeteners, aromas etc.

Fillers can be selected from (but not limited to) lactose in different forms (anhydrous, monohydrate, spray dried lactose etc.), microcrystalline cellulose, powdered cellulose, silicified microcrystalline cellulose, starches, calcium phosphate, calcium hydrogen phosphate, calcium carbonate, sucrose, glucose, fructose, dextrates, maltodextrins, other sugars such as mannitol, lactitol, xylitol, sorbitol, calcium lactate or combined fillers. The pharmaceutical formulations of the invention preferably contain 60-80% of lactose monohydrate and 15-30% of microcrystalline cellulose.

The pharmaceutical formulations of the present invention may also comprise binders such as povidone, microcrystalline cellulose, hydroxyethyl cellulose, hydroxypropyl cellulose, low substituted hydroxypropyl cellulose, hydroxypropylmethyl cellulose or other cellulose ethers, starch, pregelated starch, gelatine, polymethacrylate, or a binder mixture.

Further, there can also be present disintegrants and/or superdisintegrants, such as starches (e.g. corn starch, potato starch), modified starches (sodium starch glycolate), modified cellulose (croscarmelose i.e. crosslinked sodiumcarboxymethyl cellulose), crosslinked polyvinylpyrrolidone (crospovidone), mycrocrystalline cellulose, sodium carboxymethyl cellulose, Amberlite®, alginic acid, sodium alginate, guar gum, gellan gum, Xanthan SM® or calcium silicate. Preferably, the auxiliaries include at least one disintegrant or superdisintegrant selected from croscarmellose, crospovidone, and mycrocrystalline cellulose. More preferably, the superdisintegrant crospovidone is used in an amount of 2-10% and yet more preferably of 4-9%.

As further excipients there can be present lubricants such as stearic acid, magnesium stearate, calcium stearate, sodium lauryl sulfate, hydrogenated vegetable oil, hydrogenated castor oil, sodium stearyl fumarate, talc, macrogols. Preferably, the excipients include at least one lubricant selected from magnesium stearate, sodium stearyl fumarate and talc.

To the composition of the invention also glidants can be added. They can be selected from the group comprising talc and silica of different types (such as colloidal or precipitated silica) etc.

The excipients may have several functions, i.e. one excipient may be a filler and an additional binder, a binder and an disintegrant etc.

For the preparation of pharmaceutical compositions according to the invention any suitable process such as direct compression, wet (aqueous or alcohol) or dry granulation etc. can be used.

In a preferred embodiment, the invention also relate to a pharmaceutical composition obtainable by a process including granulating a mixture of excipients with a solution comprising perindopril or a salt thereof and an inorganic calcium salt.

The inorganic calcium salt is preferably calcium chloride. The solvent is in particular water or a mixture of water and ethanol.

The pharmaceutical compositions are usually present in a package with a blister package being preferable. The compositions can be closed in a material substantially nonpermeable for gas exchange, such as a package having an atmosphere with the required reduced oxygen content.

Preferably, the package substantially nonpermeable for gas exchange is selected from the group consisting of Al/Al blister, Al-polychloro-3-fluoroethylene homopolymer/PVC laminate blister or a bottle.

The present invention is illustrated by the following Examples without being limited to them.

EXAMPLES

Preparation of Perindopril Erbumine

Example 1

2-methylpropane-2-amine salt of perindopril (2S, 3aS,7aS)-1-((2S)-2-(((1R)-1-ethoxycarbonyl)butyl) amino-1-oxopropyl)octahydro-1H-indole-2-carboxylic acid) or perindopril erbumine To (2S,3aS,7aS)-octahydroindole-2-carboxylic acid (7.44 g) in dichloromethane (80 mL) at 20-25° C., trimethylchlorosilane (5.84 mL) and triethylamine (6.4 mL) were added and it was stirred at 20-25° C. for two hours. After two hours triethylamine (5.54 mL) was added, the suspension was cooled to −15° C., a suspension of N—((S)-1-carbetoxybutyl)-L-alanylchloride hydrochloride (11 g) in dichloromethane (80 mL), cooled to −15° C., was poured thereto and the stirring was continued at a temperature from 0° C. to −5° C. for two hours. The reaction solution was heated to 0° C., the precipitated triethylamine hydrochloride was filtered off and washed with dichloromethane (20 mL), water (66 mL) in which NaOH (1.6 g) had been dissolved was added to the filtrate and the pH was adjusted to 4.2 with a 20% NaOH solution. The organic phase was separated and the aqueous layer was washed two more times with dichloromethane (40 mL). The combined dichloromethane layers were evaporated, the residue was dissolved in isopropyl acetate (250 mL), the undissolved part was filtered off, and t-butylamine (4.4 mL) was added to the filtrate. The precipitated crystals were dissolved at the boiling point of the solution, the clear solution was cooled to 10-20° C. and it was continued with stirring for two hours. After two hours, the precipitated crystals were filtered off, washed with isopropyl acetate (30 mL) and dried at 35-40° C. in an air dryer. 15.3 g of perindopril erbumine in alpha form with a purity of more than 99% were obtained; the content of single impurities was not above 0.1%.

Example 2

Perindopril Erbumine

To a suspension of (2S,3aS,7aS)-octahydro-1H-indole-2-carboxylic acid (1.86 g; 0.011 M) in dichloromethane (40 mL), there were added trimethylchlorosilane (2.93 mL; 0.22 M) and triethylamine (3.07 mL; 0.022 M) and it was continued with stirring for 3 hours at 20-25° C. After 3 hours to the suspension cooled to −10° C. a cooled solution of previously prepared activated N—((S)-1-carbetoxybutyl)-(S)-alanine was added, which had been prepared to the following manner:

A solution of N—((S)-1-carbethoxybutyl)-(S)-alanine (2.17 g; 0.01 M) and imidazole (2.73 g; 0.04 M) in dichloromethane (40 mL) was cooled to −10° C. and thionyl chloride (0.76 mL; 0.0115 M) was added thereto and it was continued with stirring for 2 hours at 20-25° C. After two hours imidazole hydrochloride was filtered off and the filtrate was cooled to −10° C. After the completed addition of activated N—((S)-1-carbetoxybutyl)-(S)-alanine, it was continued with stirring for 3 hours at −10° C. and then for another 18 hours at 20-25° C. After completed reaction water (25 mL) was added thereto, the pH was adjusted to 5-6 with a 20% NaOH solution, the layers were separated and the aqueous layer was extracted two more times with dichloromethane (15 mL). The volatile components of the combined organic layers were evaporated, the oily residue was suspended in acetonitrile (75 mL), the undissolved part was filtered off and t-butylamine (1.11 mL; 0.01 M) was added to the filtrate. The suspension was heated to the boiling point of the solution, the clear solution was cooled to 20-25° C. and the precipitated crystals were filtered off. After drying at 40-45° C., 2.69 g of perindopril erbumine were obtained.

Example 3

Perindopril Erbumine

Perindopril erbumine (6.0 g) was dissolved in the solvent mixture of ethyl acetate (90 mL) and water (1.2 mL) and tert-butylamine (0.1 mL) was added thereto. The reaction mixture was heated to the reflux. The solution was cooled to room temperature and macerated at room temperature overnight. It was cooled to 3° C. and macerated for two more hours at this temperature. The cooled precipitate was filtered off and crushed well on the filter. The well-crushed product was dried in a vacuum dryer at 40° C. overnight. 5.48 g (91%) of perindopril erbumine (KF=0.82%) were obtained.

("KF" refers to the water content determined according to Karl Fischer)

Example 4

Perindopril Erbumine

Perindopril erbumine (3.0 g) was dissolved in the solvent mixture of isopropyl acetate (45 mL) and water (0.6 mL). The reaction mixture was heated to reflux. The solution was cooled to room temperature and macerated at room temperature overnight. It was cooled to −10° C. and macerated for four more hours at this temperature. The cooled precipitate was filtered off and crushed well on the filter. The filtered-off product was dried in a vacuum dryer at 40° C. overnight. 2.81 g (93%) of perindopril erbumine (KF=0.85%) were obtained.

Preparation of Perindopril

Example 5

Preparation of Perindopril from Perindopril Erbumine

Perindopril erbumine (151.2 g) was suspended in ethanol (1500 mL), $H_2SO_4$ (11.2 mL) was added dropwise at 20-25° C. and it was continued with stirring for 1.5 hours. The precipitate was filtered off and the filtrate was evaporated. To the oily residue dichloromethane (625 mL) and water (625 mL) were added and the pH was adjusted to 4.2 with a 10% NaOH solution. The organic layer was separated and the aqueous layer was again extracted with dichloromethane (500 mL). The combined organic layers were evaporated and 125.3 g of a foamy residue of perindopril were obtained.

Example 6

Preparation of Perindopril from Perindopril Erbumine with $CaCl_2$

Perindopril erbumine (5.5 g) was suspended in ethyl acetate (82 mL), calcium chloride hexahydrate (1.375 g) was added thereto and the suspension was heated to the boiling point of the suspension. The suspension was cooled to 20-25° C. and it was continued with stirring for 2 hours. The precipitate was filtered off, water (40 mL) was added to the filtrate, the pH was adjusted to 5, the layers were separated and the aqueous layer was again extracted with ethyl acetate (40 mL). The combined ethyl acetate layers were evaporated and 3.27 g of a foamy residue of perindopril were obtained.

Preparation of Amine Salts of Perindopril

Example 7

Preparation of Cyclohexylamine Salt of Perindopril

Perindopril (88.34 g) obtained according to the above-described process (synthesis of Example 1 or 2, wherein, subsequent to extraction, dichloromethane layers were combined and evaporated) was dissolved in acetonitrile (1700 ml), cyclohexylamine (29 mL) was added thereto and the suspension was heated to the boiling point of the solution. The clear solution was cooled to 20-25° C. and it was continued with stirring for further two hours, the precipitated crystals were filtered off, washed with 2×200 mL of acetonitrile and dried in a vacuum dryer at 40° C. 93 g of cyclohexylamine salt of perindopril, HPLC purity 99.8%, were obtained.

Example 8

Preparation (±) Sec-Butylamine Salt of Perindopril

Perindopril (41.6 g) obtained according to the above-described process (synthesis according to Example 1 or 2, wherein, subsequent to extraction, dichloromethane layers were combined and evaporated) was dissolved in acetonitrile (627 mL) and (±) sec-butylamine salt (11.48 mL) was added thereto and the suspension was heated to the boiling point of the solution. The clear solution was cooled to 20-25° C. and it was continued with stirring overnight. The suspension was cooled to 10-15° C., the precipitated crystals were filtered off, washed with 100 mL of cooled acetonitrile and dried. 43 g of (±) sec-butylamine salt of perindopril, HPLC purity 99.9%, were obtained.

Example 9

Preparation of Cyclopentylamine Salt of Perindopril

Perindopril (41.6 g) obtained according to the above-described process was dissolved in acetonitrile (627 mL), cyclopentylamine (11.2 mL) was added thereto, and the suspension was heated to the boiling point of the solution. The clear solution was cooled to 20-25° C. and it was continued with stirring overnight. The suspension was cooled to 10-15° C., the precipitated crystals were filtered off and washed with 100 mL of cooled acetonitrile. They were again suspended in acetonitrile (310 mL) and the precipitate was filtered off and dried. 20 g of cyclopentylamine salt of perindopril, HPLC purity 99.9%, were obtained.

Example 10

Preparation of Cycloheptylamine Salt of Perindopril

Perindopril (41.6 g) obtained according to the above-described process was dissolved in acetonitrile (627 mL), cycloheptylamine (14.47 mL) was added thereto, and the suspension was heated to the boiling point of the solution. The clear solution was cooled to 20-25° C. and it was continued with stirring overnight. The suspension was cooled to 10-15° C., the precipitated crystals were filtered off, washed with 100 mL of cooled acetonitrile and dried. 49.7 g of cycloheptylamine salt of perindopril, HPLC purity 99.9%, were obtained.

Preparation of Ca Salt of Perindopril

Example 11

Preparation of Calcium Salt of Perindopril Hydrochloride

Perindopril erbumine (110 g) was suspended in ethyl acetate (1650 mL), calcium chloride hexahydrate (27.5 g) was added thereto, and the suspension was heated to the boiling point of the suspension. The suspension was cooled to 20-25° C. and it was continued with stirring overnight. The precipitate was filtered off, the filtrate was evaporated, the oily residue was dissolved in ethyl acetate (1500 mL), and hydrogen chloride (10.2 g) was introduced into the solution. After two hours of stirring at 20-25° C., the precipitate was filtered off, washed with ethyl acetate (100 mL) and dried in vacuum. 96.5 g of calcium salt of perindopril hydrochloride, HPLC purity 99.4%, were obtained.

Example 12

Preparation of Calcium Salt of Perindopril

Perindopril erbumine (5.5 g) was suspended in ethyl acetate (82 mL), calcium chloride hexahydrate (1.375 g) was added thereto, and the suspension was heated to the boiling point of the suspension. The suspension was cooled to 20-25° C. and it was continued with stirring overnight. The precipitate was filtered off and the filtrate was evaporated. 4.9 g of a glassy calcium salt of perindopril were obtained.

Preparation of Polymorphic Form M1 of Perindopril Erbumine

Example 13

Perindopril erbumine (10 g) was macerated in acetonitrile (100 mL) for 10 hours and thereafter the product was filtered off.

Example 14

Perindopril erbumine (10 g) was macerated in ethyl acetate (100 mL) for 10 hours and thereafter the product was filtered off.

Preparation of Polymorphic Form M2 of Perindopril Erbumine

Example 15

Polymorphic form M1 was stored under closed conditions at room temperature for 7 months.

The following are examples of formulations with new salts of perindopril according to the invention.

Formulations with Perindopril Erbumine

|  | F1 Amount (mg/tablet) | F2 Amount (mg/tablet) |
|---|---|---|
| Perindopril erbumine | 4.00* | 4.00* |
| Microcrystalline cellulose | 22.50 | 22.50 |
| Lactose monohydrate | 63.26 | 63.78 |
| Crospovidone | 8.00 | 8.00 |
| Sodium hydrogen carbonate | 1.52 | — |
| Calcium chloride hexahydrate | — | 1.00 |
| Colloidal silica, anhydrous | 0.27 | 0.27 |
| Magnesium stearate | 0.45 | 0.45 |
| Tablet weight | 100.00 | 100.00 |

*corresponds to 3.34 mg of perindopril

Example F1

The formulation was prepared by wet granulation. A mixture of microcrystalline cellulose, lactose and crospovidone was granulated with a water or an ethanol-water solution of perindopril erbumine and sodium hydrogen carbonate in a molar ratio of 1:2.

Example F2

The formulation was prepared by wet granulation. A mixture of microcrystalline cellulose, lactose and crospovidone was granulated with a water or an ethanol-water solution of perindopril erbumine and calcium chloride in a molar ratio of 2:1. The granulation liquid was prepared in such a way that perindopril erbumine and calcium chloride in a molar ratio of 2:1 were added to water or an ethanol-water solution and it was stirred until a clear solution appeared.

|  | F2a Amount (mg/tablet) |
|---|---|
| Perindopril erbumine | 8.00* |
| Microcrystalline cellulose (Avicel PH112) | 45.00 |
| Lactose monohydrate | 127.16 |
| Crospovidone | 16.00 |
| Calcium chloride hexahydrate | 2.40 |
| Colloidal silica, anhydrous | 0.54 |
| Magnesium stearate | 0.90 |
| Tablet weight | 200.00 |

*corresponds to 6.68 mg of perindopril

Example F2a

The formulation was prepared by wet granulation. A mixture of lactose and crospovidone was granulated with a water solution of perindopril erbumine and calcium chloride. The granulation liquid was prepared in such a way that perindopril erbumine and calcium chloride were added to water and it was stirred until a clear solution appeared. Prepared granulate was mixed with microcrystalline cellulose and colloidal silica. Magnesium stearate was added to the mixture and finally mixed. Then tabletting mixture was pressed on a tabletting machine.

Formulations with Calcium Salt of Perindopril Hydrochloride

|  | F3 Amount (mg/tablet) | F4 Amount (mg/tablet) |
|---|---|---|
| Calcium salt of perindopril hydrochloride | 3.84* | 3.84* |
| Microcrystalline cellulose | 22.50 | 22.50 |
| Lactose monohydrate | 66.42 | 71.42 |
| Crospovidone | 5.00 | — |
| Sodium hydrogen carbonate | 1.52 | 1.52 |
| Colloidal silica, anhydrous | 0.27 | 0.27 |
| Magnesium stearate | 0.45 | 0.45 |
| Tablet weight | 100.00 | 100.00 |

*corresponds to 3.34 mg of perindopril

Example F3

The formulation was prepared by wet granulation. A mixture of microcrystalline cellulose, lactose and crospovidone was granulated with a water or an ethanol-water solution of calcium salt of perindopril hydrochloride and sodium hydrogen carbonate in a molar ratio of 1:4.

Example F4

The formulation was prepared by direct tabletting. Calcium salt of perindopril hydrochloride, microcrystalline cellulose, lactose, sodium hydrogen carbonate, colloidal silica and magnesium stearate were homogeneously mixed.

Formulation with Calcium Salt of Perindopril

|  | F5 Amount (mg/tablet) |
| --- | --- |
| Calcium salt of perindopril | 3.52* |
| Microcrystalline cellulose | 22.50 |
| Lactose monohydrate | 73.26 |
| Colloidal silica, anhydrous | 0.27 |
| Magnesium stearate | 0.45 |
| Tablet weight | 100.00 |

*corresponds to 3.34 mg of perindopril

Example F5

The formulation was prepared by direct tabletting. Calcium salt of perindopril, microcrystalline cellulose, lactose monohydrate, anhydrous colloidal silica and magnesium stearate were homogeneously mixed.

Formulation with Cyclohexylamine Salt of Perindopril

|  | F6 Amount (mg/tablet) |
| --- | --- |
| Cyclohexylamine salt of perindopril | 4.24* |
| Microcrystalline cellulose | 22.50 |
| Lactose monohydrate | 70.05 |
| Sodium hydrogen carbonate | 0.76 |
| Talc | 2.00 |
| Magnesium stearate | 0.45 |
| Tablet weight | 100.00 |

*corresponds to 3.34 mg of perindopril; as amine salt of perindopril, any salt according to the present invention in an amount corresponding to 3.34 mg of perindopril can be used.

Example F6

The formulation was prepared by direct tabletting. Cyclohexylamine salt of perindopril, an equimolar amount of sodium hydrogen carbonate, microcrystalline cellulose, lactose, talc and magnesium stearate were homogeneously mixed.

Formulations with Perindopril Erbumine and Indapamide

|  | F7 Amount (mg/tablet) | F8 Amount (mg/tablet) |
| --- | --- | --- |
| Perindopril erbumine | 2.000* | 4.00* |
| Indapamide | 0.625 | 1.25 |
| Microcrystalline cellulose (Avicel PH112) | 11.250 | 22.50 |
| Lactose monohydrate | 31.165 | 62.33 |
| Crospovidone | 4.000 | 8.00 |
| Calcium chloride hexahydrate | 0.600 | 1.20 |
| Colloidal silica, anhydrous | 0.135 | 0.27 |
| Magnesium stearate | 0.225 | 0.45 |
| Tablet weight | 50.00 | 100.00 |

*corresponds to 1.67 mg of perindopril or 3.34 mg of perindopril respectively

Example F7 and F8

The formulation was prepared by wet granulation. A mixture of indapamide, lactose and crospovidone was granulated with a water solution of perindopril erbumine and calcium chloride. The granulation liquid was prepared in such a way that perindopril erbumine and calcium chloride were added to water and it was stirred until a clear solution appeared. Prepared granulate was mixed with microcrystalline cellulose and colloidal silica. Magnesium stearate was added to the mixture and finally mixed. The tabletting mixture was pressed on a tabletting machine.

|  | F7a Amount (mg/tablet) | F8a Amount (mg/tablet) |
| --- | --- | --- |
| Perindopril erbumine | 2.000* | 4.00* |
| Indapamide | 0.625 | 1.25 |
| Microcrystalline cellulose (Avicel PH112) | 11.250 | 22.50 |
| Lactose monohydrate | 31.165 | 62.33 |
| Crospovidone | 4.000 | 8.00 |
| Calcium chloride hexahydrate | 0.600 | 1.20 |
| Colloidal silica, anhydrous | 0.135 | 0.27 |
| Magnesium stearate | 0.225 | 0.45 |
| Tablet weight | 50.00 | 100.00 |

*corresponds to 1.67 mg of perindopril or 3.34 mg of perindopril respectively

Example F7a and F8a

The formulation was prepared by wet granulation. A mixture of lactose and crospovidone was granulated with a water solution of perindopril erbumine and calcium chloride. The granulation liquid was prepared in such a way that perindopril erbumine and calcium chloride were added to water and it was stirred until a clear solution appeared. Prepared granulate was homogeneously mixed with indapamide, microcrystalline cellulose and colloidal silica. Magnesium stearate was added to the mixture and finally mixed. The tabletting mixture was pressed on a tabletting machine.

Formulations with Perindopril Erbumine and Amlodipine Besylate

|  | F9 Amount (mg/tablet) |
| --- | --- |
| Perindopril erbumine | 4.00* |
| Amlodipine besylate | 6.94** |
| Sodium hydrogen carbonate | 0.50 |
| Microcrystalline cellulose (Avicel PH112) | 22.50 |
| Lactose monohydrate | 56.14 |
| Crospovidone | 8.00 |
| Calcium chloride hexahydrate | 1.20 |
| Colloidal silica, anhydrous | 0.27 |
| Magnesium stearate | 0.45 |
| Tablet weight | 100.00 |

*corresponds to 3.34 mg of perindopril
**corresponds to 5 mg of amlodipine

Example F9

The formulation was prepared by wet granulation. A mixture of lactose and crospovidone was granulated with a water solution of perindopril erbumine and calcium chloride. The granulation liquid was prepared in such a way that perindopril erbumine and calcium chloride were added to water and it was stirred until a clear solution appeared. Prepared granulate was mixed with amlodipine besylate, microcrystalline cellulose, sodium hydrogen carbonate and colloidal silica, anhydrous. Magnesium stearate was added to the mixture and finally mixed. The tabletting mixture was pressed on a tabletting machine.

One can also use calcium hydrogen phosphate, anhydrous (DiCafos A) or any other basic stabilizing agent instead of sodium hydrogen carbonate in order to adjust pH of the tablet. Other strenghts of perindopril erbumine/amlodipine 4 mg/10 mg, 8 mg/5 mg and 8 mg/10 mg are also possible by adjusting the amount of lactose monohydrate in order to correct tablet weight.

|  | F10 Amount (mg/tablet) |
| --- | --- |
| Perindopril erbumine | 4.00* |
| Amlodipine besylate | 6.94** |
| Microcrystalline cellulose | 22.50 |
| Lactose monohydrate | 65.34 |
| Sodium hydrogen carbonate | 0.50 |
| Colloidal silica, anhydrous | 0.27 |
| Magnesium stearate | 0.45 |
| Tablet weight | 100.00 |

*corresponds to 3.34 mg of perindopril
**corresponds to 5 mg of amlodipine

Example F10

The formulation was prepared by direct tabletting. Perindopril erbumine, amlodipine besylate, sodium hydrogen carbonate, microcrystalline cellulose, anhydrous lactose and anhydrous colloidal silica were homogeneously mixed. Magnesium stearate was added and finally mixed. The obtained tabletting mixture was pressed into tablets.

One can also use calcium hydrogen phosphate, anhydrous (DiCafos A) instead of sodium hydrogen carbonate in order to adjust pH of the tablet. Other strenghts of perindopril erbumine/amlodipine 4 mg/10 mg, 8 mg/5 mg and 8 mg/10 mg are possible by adjusting the amount of lactose monohydrate in order to correct tablet weight.

|  | F11 Amount (mg/tablet) |
| --- | --- |
| Perindopril erbumine | 4.00* |
| Amlodipine besylate | 6.94** |
| Microcrystalline cellulose (Avicel PH200 LM) | 128.71 |
| Pregelatinised starch (Starch 1500) | 27.00 |
| Sodium starch glycolate (Type A) | 11.00 |
| Colloidal silica, anhydrous | 0.55 |
| Magnesium stearate | 1.80 |
| Tablet weight | 180.00 |

*corresponds to 3.34 mg of perindopril
**corresponds to 5 mg of amlodipine

Example F11

The formulation was prepared by direct tabletting. Perindopril erbumine, amlodipine besylate, microcrystalline cellulose, pregelatinised starch, sodium starch glycolate and anhydrous colloidal silica were homogeneously mixed. At the end magnesium stearate was added and mixed. The tabletting mixture was pressed into tablets. Other strenghts of perindopril erbumine/amlodipine 4 mg/10 mg, 8 mg/5 mg and 8 mg/10 mg are possible by adjusting the amount of lactose monohydrate in order to correct tablet weight.

The invention claimed is:
1. A calcium salt of perindopril or a solvate thereof.
2. A calcium salt according to claim 1, which is in form of an acid addition salt thereof with an organic or inorganic acid.
3. A calcium salt according to claim 2, wherein the organic or inorganic acid is selected from the group of HCl, HBr, HI, maleic acid and fumaric acid.
4. A calcium salt of perindopril hydrochloride.
5. An alkyl amine salts of perindopril represented by the structural formula

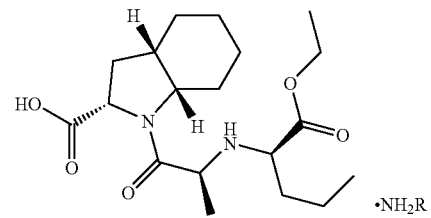

wherein R represents $C_5$-$C_7$ cycloalkyl or solvate thereof.
6. A cyclopentylamine salt of perindopril characterised by an X-ray powder diffraction pattern having peaks 2Θ/° at about 8.1, 9.2, 16.9, 19.1, 19.8, 21.3, 22.8, 24.4±0.2.
7. A cyclohexylamine salt of perindopril characterised by an X-ray powder diffraction pattern having peaks 2Θ/° at about 4.1, 8.1, 9.3, 15.2, 18.8, 21.1, 22.2, 24.3±0.2.
8. A cycloheptylamine salt of perindopril characterised by an X-ray powder diffraction pattern having peaks 2Θ/° at about 4.0, 9.0, 14.1, 15.2, 16.8, 18.1, 21.0, 24.1±0.2.
9. A sec.-butylamine salt of perindopril characterised by an X-ray powder diffraction pattern having peaks 2Θ/° at about 5.0, 8.6, 9.3, 15.3, 20.4, 20.8, 22.4, 24.2, 26.1±0.2.
10. A salt according to claim 1 for use as medicament for the treatment of hypertension and cardial insufficiency.
11. A pharmaceutical composition comprising a salt according to claim 1.
12. The pharmaceutical composition of claim 11 obtainable by a process including granulating a mixture of excipients with a solution comprising perindopril or a salt thereof and an inorganic calcium salt.
13. A pharmaceutical composition according to claim 12, wherein the solution includes water or a mixture of water and ethanol as solvent.
14. The pharmaceutical composition of claim 12, wherein the inorganic calcium salt is calcium chloride.
15. A salt according to claim 5 for use as medicament for the treatment of hypertension and cardial insufficiency.
16. A salt according to claim 6 for use as medicament for the treatment of hypertension and cardial insufficiency.
17. A salt according to claim 7 for use as medicament for the treatment of hypertension and cardial insufficiency.
18. A salt according to claim 8 for use as medicament for the treatment of hypertension and cardial insufficiency.
19. A salt according to claim 9 for use as medicament for the treatment of hypertension and cardial insufficiency.

* * * * *